US012673914B2

(12) United States Patent
Srinivas et al.

(10) Patent No.: US 12,673,914 B2
(45) Date of Patent: Jul. 7, 2026

(54) CONTINUOUS PROCESS FOR THE SYNTHESIS OF DIMETHYL CARBONATE OVER A CERIUM-BASED CATALYST FORMULATION

(71) Applicant: COUNCIL OF SCIENTIFIC AND INDUSTRIAL RESEARCH, New Delhi (IN)

(72) Inventors: Darbha Srinivas, Pune (IN); Vijay Vasant Bokade, Pune (IN); Prashant Suresh Niphadkar, Pune (IN); Unnikrishnan Pulikkeel, Pune (IN); Snehalkumar Parmar, Moti Khavdi (IN); Vinay Amte, Moti Khavdi (IN); Surajit Sengupta, Moti Khavdi (IN); Asit Kumar Das, Moti Khavdi (IN)

(73) Assignee: Council of Scientific and Industrial Research, New Delhi (IN)

( * ) Notice: Subject to any disclaimer, the term of this patent is extended or adjusted under 35 U.S.C. 154(b) by 461 days.

(21) Appl. No.: 18/273,834

(22) PCT Filed: Jan. 25, 2022

(86) PCT No.: PCT/IN2022/050056
§ 371 (c)(1),
(2) Date: Jul. 24, 2023

(87) PCT Pub. No.: WO2022/162688
PCT Pub. Date: Aug. 4, 2022

(65) Prior Publication Data

US 2024/0101506 A1 Mar. 28, 2024

(30) Foreign Application Priority Data

Jan. 26, 2021 (IN) ............................ 202111003498

(51) Int. Cl.

| | |
|---|---|
| ***C07C 68/04*** | (2006.01) |
| ***B01J 23/10*** | (2006.01) |
| ***B01J 35/37*** | (2024.01) |
| ***B01J 35/50*** | (2024.01) |
| ***B01J 35/61*** | (2024.01) |
| ***B01J 35/63*** | (2024.01) |
| ***B01J 37/04*** | (2006.01) |
| ***B01J 37/06*** | (2006.01) |
| ***B01J 37/08*** | (2006.01) |

(52) U.S. Cl.
CPC ............... *C07C 68/04* (2013.01); *B01J 23/10* (2013.01); *B01J 35/37* (2024.01); *B01J 35/50* (2024.01); *B01J 35/615* (2024.01); *B01J 35/633* (2024.01); *B01J 37/04* (2013.01); *B01J 37/06* (2013.01); *B01J 37/08* (2013.01); *B01J 2235/00* (2024.01); *B01J 2235/30* (2024.01)

(58) Field of Classification Search
CPC ........ C07C 68/04; B01J 35/615; B01J 35/633
See application file for complete search history.

(56) References Cited

U.S. PATENT DOCUMENTS 9,073,849 B2 7/2015 Srinivas et al.

FOREIGN PATENT DOCUMENTS

| | | |
|---|---|---|
| CN | 110882686 | 3/2020 |
| WO | WO 2016/151602 | 9/2016 |

OTHER PUBLICATIONS

Atul Bansode et al., Continuous DMC Synthesis from CO2 and Methanol over a CeO2 Catalyst in a Fixed Bed Reactor in the Presence of a Dehydrating Agent ACS Catal. 2014, 4, 3877-3880 (Year: 2014).*

Bansode, A., et al, Continuous DMC Synthesis from CO2 and Methanol over a CeO2 Catalyst in a Fixed Bed Reactor in the Presence of a Dehydrating Agent ACS Catalysis V4, Is 11, 3877-3880 (Year: 2014).*

Bansode et al., "Continuous DMC Synthesis from $CO_2$ and Methanol over a $CeO_2$ Catalyst in a Fixed Bed Reactor in the Presence of a Dehydrating Agent" *ACS Catalysis* 2014, 4, 3877-3880.

Indian Application No. 1559/DEL/2012—"Process for Making Di-Methyl Carbonate", Dec. 4, 2015, IN1559/DEL/2012 "Process for Making Di-Methyl Carbonate" (wipo.int).

Indian Application No. 2734/DEL/2014—"An Improved Process for Preparing Dimethyl Carbonate", Aug. 31, 2016, IN2734/DEL/2014 "An Improved Process for Preparing Dimethyl Carbonate" (wipo.int).

* cited by examiner

*Primary Examiner* — Samantha L Shterengarts
*Assistant Examiner* — Ernesto Valle
(74) *Attorney, Agent, or Firm* — Norton Rose Fulbright US LLP

(57) ABSTRACT

The present invention discloses a continuous process for the synthesis of dimethyl carbonate from methanol and carbon dioxide over a ceria-based mixed metal oxide-silica catalyst formulation in the presence of a dehydrating or water trapping compound (2-Cyanopyridine).

14 Claims, 5 Drawing Sheets

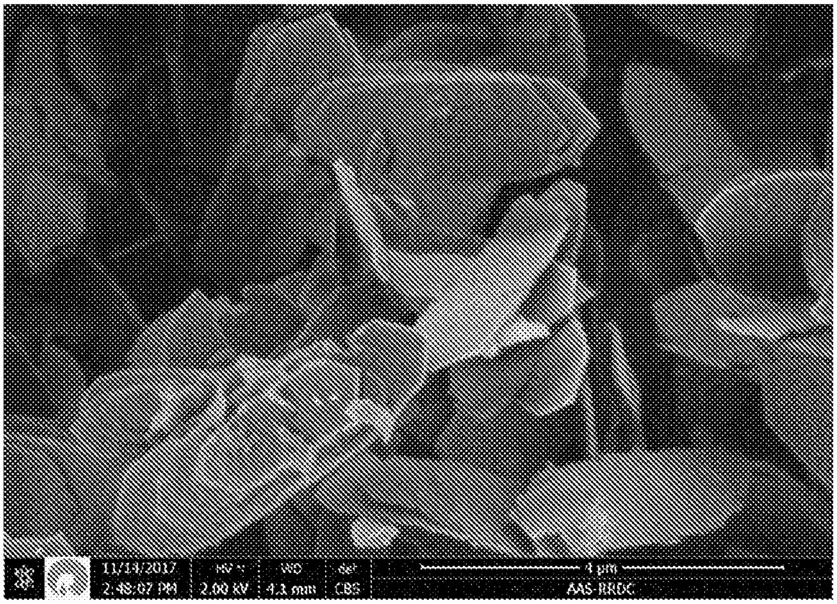
Fig: 8

CONTINUOUS PROCESS FOR THE SYNTHESIS OF DIMETHYL CARBONATE OVER A CERIUM-BASED CATALYST FORMULATION

CROSS-REFERENCE TO RELATED APPLICATIONS

This application is a national phase application under 35 U.S.C. § 371 of International Application No. PCT/IN2022/050056 filed 25 Jan. 2022, which claims priority to Indian Patent Application number 202111003498 filed 26 Jan. 2021. The entire contents of each of the above-referenced disclosures is specifically incorporated herein by reference without disclaimer.

FIELD OF THE INVENTION

The present invention relates to a continuous process for the synthesis of dimethyl carbonate (DMC) over a cerium-based catalyst formulation. More particularly, the present invention relates to a $CeO_2$-based mixed metal oxide supported on silica compound as a catalyst for the continuous production of DMC from methanol and $CO_2$.

BACKGROUND AND PRIOR ART OF THE INVENTION

Dimethyl carbonate (DMC) is an industrially important, environmentally benign chemical having applications as methylating agent, carbonylation agent, oxygenate fuel additive (substituent to methyl-tertiary butylether; MTBE), solvent and electrolyte in Li-ion batteries. DMC replaces toxic phosgene ($COCl_2$) in manufacturing polyurethanes and polycarbonates. Its direct synthesis from methanol and $CO_2$ is more advantageous than its traditional methods of synthesis viz. phosgenation and oxidative carbonylation of methanol, which are associated with the risks of toxicity or hazardous nature. Utilization of $CO_2$ as feedstock in chemicals and fuels manufacturing can have positive impact on environment as it can lead to low carbon footprint technologies and reduced global warming. Despite these advantages, this simple, green, atom-efficient, $CO_2$-based direct synthesis approach for DMC is not commercialized till date as it suffers from equilibrium and thermodynamic limitations [Eq. (1)].

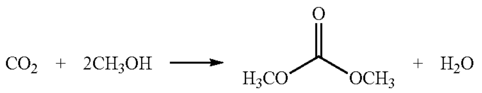

$\Delta G_{25° C.} = +26.21$ kJ/mol

Equimolar amount of water is co-produced (with DMC) in the reaction, which should be taken out instantaneously to swing the equilibrium to right side so as to improve DMC yield. Instantaneous removal of water in the reaction is desired at it can interact and deactivate the catalyst. Development of an efficient, solid catalyst that activates methanol and $CO_2$ simultaneously and a method that removes water in the reaction instantly are crucial to overcome the thermodynamic and kinetic limitations and catalyst deactivation of the direct DMC synthesis reaction. A continuous DMC manufacturing process is economically beneficial than a batch process.

Indian patent application IN201402734I1 (2734DEL2014) discloses an improved batch process for preparing DMC comprising reaction of methanol with $CO_2$ in presence of a water trapping agent selected from the group of molecular sieves and nitrile group containing compounds such as acetonitrile, benzonitrile and cyanopyridines and a ceria-metal oxide solid solution catalyst of "spindle shape" morphology having molecular formula of $Ce_{1-x}M_xO_{2-\delta}$, where the value of x is in the range of 0.05 to 0.8 and 6 is in the range of 0 to 0.8. DMC yield of greater than 65 mol % (at 150° C. after 2 h of reaction) was reported. Use and stability of this catalyst in a continuous process was not disclosed.

U.S. Pat. No. 9,073,849 and Indian patent IN302623B unveil a batch reactor process for making DMC from methanol with $CO_2$ in presence of a solid, calcinied catalyst derived from zirconium phosphonate having molecular formula: $Zr(X)_{2-n}Y_n{\cdot}mH_2O$, where X refers to phosphonate, Y refers to $HPO_4^{2-}$ or $HPO_3^{2-}$, n varies from 0.2 to 1.8 and m varies from 0 to 5. N,N-dimethyl formamide as solvent and molecular sieve-3 A as water trapping agent were employed. Methanol conversion of 31.8% and DMC yield of 26 mmol per gram of catalyst were reported in the batch reaction at 170° C. after 12 h.

A continuous DMC manufacturing process is economically beneficial for its large-scale industrial exploitation than a batch process. Catalyst recycle study in batch, stirred tank, slurry reactors doesn't offer indisputable evidence for catalyst stability as a continuous (fixed-bed) process does. In view of the commercial importance and development of sustainable technologies, it is, obligatory to discover stable catalyst formulations for application in continuous production of DMC from methanol and $CO_2$.

The prior-arts for making DMC by the direct synthesis route suffer from several disadvantages. They are mostly batch processes using powder catalysts. Even if there are some reports involving continuous processes using supported catalysts, the selectivity and yield of DMC in those reactions were low or the catalyst was unstable and exhibited deactivation in the time-on-stream study.

In view of the importance of DMC in industrial applications and drawbacks of prior-art processes which include low yield, low selectivity (due to formation of undesired dimethyl ether) and catalyst instability, it is desirable to have a stable, solid catalyst formulation and continuous process using such a catalyst.

Objectives of the Invention

Main objective of the present invention is to provide a continuous process for the preparation of DMC from methanol and $CO_2$ by using formulated ceria-based mixed metal oxide supported on silica compound as a catalyst.

Another objective of the present invention is to provide a stabilized, formulated ceria-based mixed metal oxide supported on silica compound as a catalyst for use in the continuous production of DMC from methanol and $CO_2$.

Yet another objective of the present invention is to provide a process for the preparation of a stabilized, formulated ceria-based mixed metal oxide supported on silica compound as a catalyst for use in the continuous production of DMC from methanol and $CO_2$.

SUMMARY OF THE INVENTION

Accordingly, the present invention provides an improved process for the synthesis of DMC, in a continuous process, comprising reacting methanol (MeOH) with carbon dioxide ($CO_2$) catalysed over an improved catalyst formulation in the presence of a dehydrating (water trapping/scavenging) compound selected from organic nitriles, more preferably 2-cyanopyridine (2-CP) to afford DMC, wherein said improved catalyst formulation comprises of: (a) mixed oxides of cerium (Ce) with other elements selected from the group consisting of zirconium (Zr), lanthanum (La), gallium (Ga) and combinations thereof, and (b) a form of silica ($SiO_2$) derived from group of silica precursors selected from group consisting of colloidal silica, ethyl silicate, ethyl orthosilicate, Si/Al combinations or like silica material, characterized in that, silica content in the catalyst formulation is between 2 and 25 weight percent, content of Ce-oxide in the mixed oxide portion is between 50 and 95 mole percent, mixed Ce-oxide possesses an elongated hexagonal, spindle-shaped, rod-like or spherical morphology and formulation is hydrophobic with water adsorption capacity not more than 10 weight percent, possesses a crush strength between 2 and 7 Newton, and stable in the continuous DMC synthesis reaction.

The molar ratio of methanol to dehydrating compound is in the range of 1:1 to 3:1.

The molar ratio of methanol to carbon dioxide is in the range of 1:3 to 2:1.

The liquid hourly space velocity of liquid feed (LHSV=volume of liquid feed per unit volume of catalyst per hour) is 0.5 to 4 $hour^{-1}$ and gas hourly space velocity of carbon dioxide (GHSV=volume of $CO_2$ per volume of catalyst per hour) is 400 to 1000 $hour^{-1}$.

The reaction temperature is in the range of 120° C. to 160° C.

The reaction pressure is in the range of 30 to 100 bar and the catalyst formulation has at least 30 hours of catalytic stability.

Yet another embodiment of the present invention provides an improved, stabilized, solid catalyst formulation essentially comprising: (a) mixed oxides of cerium (Ce) with other elements selected from the group consisting of zirconium (Zr), lanthanum (La), gallium (Ga) and combinations thereof and theses metal oxides are having an elongated hexagonal, spindle-shaped, rod-like or spherical morphology respectively, and (b) a form of silica ($SiO_2$) derived from a group of silica precursors selected from group consisting of colloidal silica, ethyl silicate, ethyl orthosilicate, Si/Al combinations or like silica material characterized in that, silica content in the catalyst formulation is between 2 and 25 weight percent, content of Ce-oxide in the mixed oxide portion is between 50 and 95 mole percent, and formulation is hydrophobic with water adsorption capacity not more than 10 weight percent, bi-functional with acidity/basicity molar ratio between 0.5 and 2.5, possesses a crush strength between 2 and 7 Newton and stable in the continuous DMC synthesis reaction.

The present invention provides the preparation method of the catalyst formulation comprising the steps of:

(a) co-precipitating precursor salt solutions of Ce and other element (Zr, La, Ga or combinations thereof) sequentially or once through at a temperature in the range of 20° C. to 30° C. using a precipitating agent, (b) mixing and ageing of the suspension of step (a) at a temperature in the range of 30° C. to 120° C., (c) filtering and water washing of the formed precipitate, (d) drying the precipitate of step (c) at 25° C. to 100° C. followed by calcination at a temperature in the range of 400° C. to 600° C. to obtain mixing oxide catalyst, and (e) mixing the mixed oxide catalyst obtained in step (d) with a silica source selected from colloidal silica, ethyl silicate, ethyl orthosilicate, Si/Al combinations and like silica source/compound and formulating and shaping of the catalyst.

ACRONYMS USED TO DESCRIBE THE INVENTION

DMC: dimethyl carbonate.
MeOH: methanol.
2-CP: 2-cyanopyridine.
LHSV: liquid hourly space velocity.
GHSV: gas hourly space velocity.
2-PA: 2-picolinamide
MPI: methyl picolinimidate.
MP: 2-methylpicolinate.
MC: methyl carbamate.

BRIEF DESCRIPTION OF THE DRAWINGS

FIG. 8: Scanning electron microscopy (SEM) image showing elongated hexagonal morphology of ceria-based mixed oxide component in Catalyst #3.

DETAILED DESCRIPTION OF THE INVENTION

Figure 1:
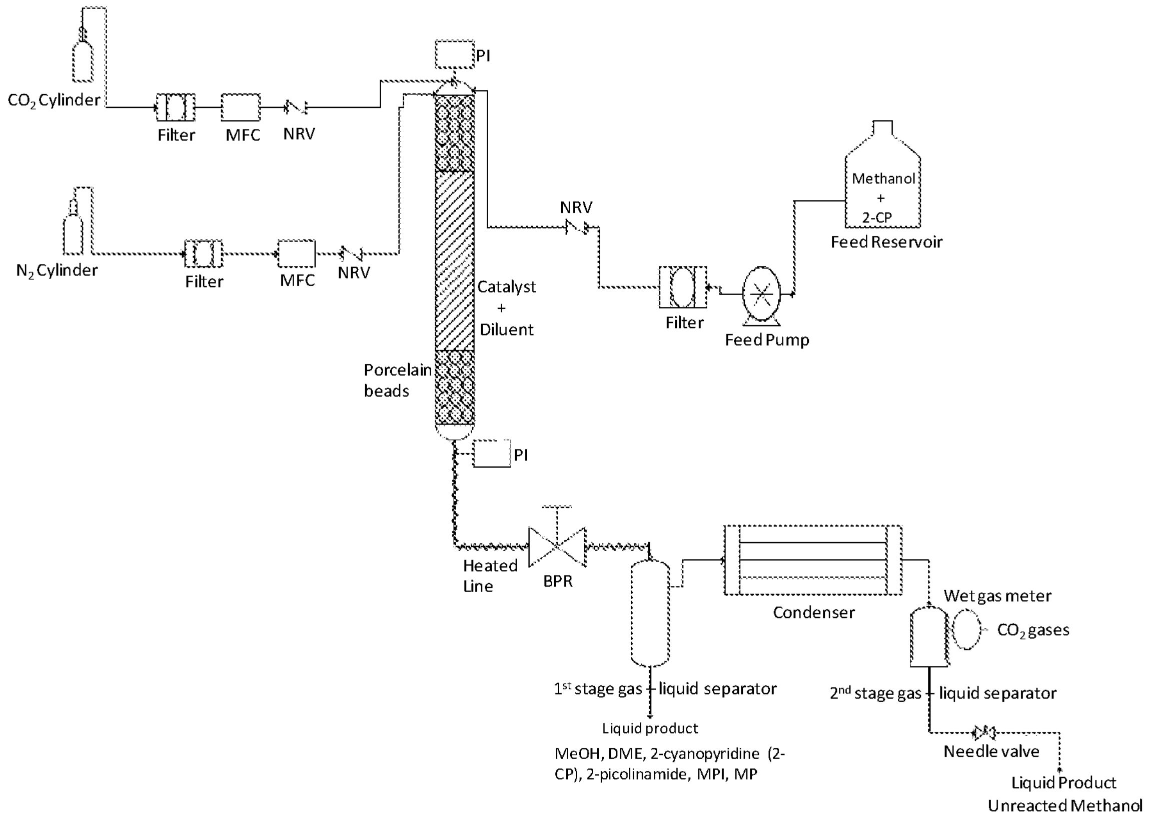
FIG. 1: Schematic process flow diagram for the reaction of methanol with $CO_2$ in a fixed-bed continuous flow reactor. Abbreviations: $CO_2$ cylinder=carbon dioxide gas cylinder, $N_2$ cylinder=nitrogen gas cylinder, MFC=mass flow controller, NRV=non return valve, PI=pressure indicator, 2-CP=2-cyanopyridine, BPR=back pressure regulator, MeOH=methanol, MPI=methyl picolinimidate, MP=2-methylpicolinate.

The invention will now be described in detail in connection with certain preferred and optional embodiments, so that various aspects thereof may be more fully understood and appreciated.

The present invention provides a process for the synthesis of DMC, in a continuous process, by contacting methanol with $CO_2$ over an improved catalyst formulation in the presence of a dehydrating or water trapping compound, wherein said improved catalyst formulation comprises of: (a) mixed oxides of cerium (Ce) with other elements selected from the group consisting of zirconium (Zr), lanthanum (La), gallium (Ga) and combinations thereof, and (b) a form of silica ($SiO_2$) derived from group of silica precursors selected from group consisting of colloidal silica, ethyl silicate, ethyl orthosilicate, Si/Al combinations or like silica material, characterized in that, silica content in the catalyst formulation is between 2 and 25 weight percent, content of Ce-oxide in the mixed oxide portion is between 50 and 95 mole percent, mixed oxide possesses an elongated hexagonal, spindle-shaped, rod-like or spherical morphology and formulation is hydrophobic with water adsorption capacity not more than 10 weight percent, possesses a crush strength between 2 and 7 Newton, and stable in the continuous DMC synthesis reaction.

The molar ratio of methanol to dehydrating agent is in the range of 1:1 to 3:1.

The molar ratio of methanol to carbon dioxide is in the range of 1:3 to 2:1.

The liquid hourly space velocity of liquid feed (LHSV=volume of liquid feed per unit volume of catalyst per hour) is 0.5 to 4 hour$^{-1}$ and gas hourly space velocity of carbon dioxide (GHSV=volume of $CO_2$ per volume of catalyst per hour) is 400 to 1000 hour$^{-1}$.

The reaction temperature is in the range of 120° C. to 160° C.

The reaction time period for stirred tank, batch reactor process is in a range of 2 to 10 hours.

The reaction pressure is in the range of 30 to 100 bar and the catalyst formulation has at least 30 hours of catalytic stability.

The dehydrating (or water trapping or water scavenging) compound is selected from organic nitrile compounds, more preferably 2-cyanopyridine (2-CP).

The carbon dioxide used in DMC synthesis reaction is 100% pure or is admixed with carbon monoxide, hydrogen and/or hydrocarbons.

Methanol used in the reaction has purity of 90 to 100%.

The continuous reaction of making DMC from methanol and $CO_2$ is performed in a fixed-bed reactor, continuous stirred tank reactor or like continuous-flow reactors.

The process for making DMC is conducted preferably in a fixed-bed continuous-flow reactor.

Dehydrating compound—2-cyanopyridine (2-CP) is converted mainly into 2-picolinamide (2-PA) and a small quantity of 2-methyl picolinate (MP) and methyl picolinimidate (MPI). Methanol conversion to dimethyl ether (DME) over the catalyst formulation is negligible (<0.2%).

The dimethyl carbonate yield in the process is above 30 mole percent.

In another embodiment, the present invention provides a stabilized, formulated ceria-based mixed metal oxide supported on silica compound as a catalyst for use in continuous production of DMC from methanol and $CO_2$.

In an embodiment, the present invention provides an improved, stabilized, solid catalyst formulation essentially comprising: (a) mixed oxides of cerium (Ce) with other elements selected from the group consisting of zirconium (Zr), lanthanum (La), gallium (Ga) and combinations thereof, and (b) a form of silica ($SiO_2$) derived from group consisting of silica precursors selected from colloidal silica, ethyl silicate, ethyl orthosilicate, Si/Al combinations or like silica material, characterized in that, silica content in the catalyst formulation is between 2 and 25 weight percent, content of Ce-oxide in the mixed oxide portion is between 50 and 95 mole percent, mixed oxide possesses an elongated hexagonal, spindle-shaped, rod-like or spherical morphology and formulation is hydrophobic with water adsorption capacity not more than 10 weight percent, possesses a crush strength between 2 and 7 Newton, and stable in the continuous DMC synthesis reaction.

The catalyst is selected from Zr—$CeO_2/SiO_2$, Zr—Ga—$CeO_2/SiO_2$, Zr—$CeO_2/Al_2O_3$, Zr—$CeO_2$, $CeO_2/SiO_2$, $CeO_2/Al_2O_3$, Zr—La—$CeO_2/SiO_2$, Ga—$CeO_2/SiO_2$, La—$CeO_2/SiO_2$, Zr—Ga—$CeO_2/SiO_2$, Zr—Ga—$CeO_2/SiO_2$—$Al_2O_3$, Ga—$CeO_2/SiO_2$—$Al_2O_3$, La—$CeO_2/SiO_2$-$Al_2O_3$ and Zr—La—$CeO_2/SiO_2$—$Al_2O_3$.

The catalyst formulation is shaped and formed into extrudates, trilobes, spheres or tablets.

The bi-functional catalyst has both acidic and basic sites on its surface with acidity/basicity molar ratio in the range of 0.5 to 2.5.

The part of cerium ions in the catalyst is in partially reduced (+3) oxidation state.

The catalyst formulation has specific surface area in the range of 100 to 300 $m^2/g$ and pore volume in the range of 0.1 to 0.35 cc/g.

In an embodiment, the present invention further provides a process for the preparation of a stabilized, formulated ceria-based mixed metal oxide supported on silica compound as a catalyst for use in continuous production of DMC from methanol and $CO_2$.

The present invention provides a process for the preparation of the above said catalyst formulation comprising the steps of:

a) co-precipitating precursor salt solutions of Ce and other element (Zr, La, Ga or combinations thereof) sequentially or once through at a temperature in the range of 20° C. to 30° C. using a precipitating agent;
b) mixing and ageing of the suspension in step (a) at a temperature in the range of 30° C. to 120° C.;
c) filtering and water washing of the formed precipitate;
d) drying the precipitate of step (c) at 25° C. to 100° C. followed by calcination at a temperature in the range of 400° C. to 600° C. to obtained mixing metal oxide, and
e) mixing the mixed oxide catalyst obtained in step (d) with a silica source selected from colloidal silica, ethyl silicate, ethyl orthosilicate, Si/Al combinations and like silica source and formulating and shaping of the catalyst.

The precipitating agent is selected from the group consisting of urea, sodium hydroxide, ammonium hydroxide, ammonium bicarbonate, tetra-alkylammonium hydroxide and such like, and more preferably ammonium bicarbonate.

The salt precursors are selected from the group consisting of $Ga(NO_3)_3{\cdot}xH_2O$, galium halide, $Ce(NO_3)_3{\cdot}6H_2O$, cerius sulphate, cerium oxalate, $ZrO(NO_3)_2{\cdot}xH_2O$, $Zr(SO_4)_2$, zirconium alkoxide, zirconium halide, lanthanum nitrate, lanthanum halide and lanthanum carbonate.

The catalyst formulation catalyzes the reaction of any alcohol with $CO_2$ forming the corresponding alkyl carbonate.

Two moles of methanol and one mole of $CO_2$ react over the catalyst to form one mole of DMC and one mole of water. The catalyst should contain acidic as well as basic sites in right strength and proportion to activate $CO_2$ and methanol to form DMC. Dehydrating compound removes water formed in the reaction. Water can compete with methanol for adsorption on the acidic sites and lead to lower DMC yields. Thus, some of the improvements and modifications contemplated include: (1) a catalyst with hydrophobic surface that can limit water adsorption on the catalyst surface and enhance DMC yield. (2) a catalyst with acid sites of moderate strength only to avoid adsorption of dehydrating compound-derived products and thereby, poisoning/deactivating the catalyst. And (3) a catalyst formulation with the support enabling optimum binding strength and doesn't alter the acid-base and adsorption properties of the oxide component.

In an embodiment of the invention it is found that a catalyst formulation comprising of: (a) mixed oxides of cerium (Ce) with other elements selected from the group consisting of zirconium (Zr), lanthanum (La), gallium (Ga) and combinations thereof, and (b) a form of silica ($SiO_2$) derived from group of silica precursors of colloidal silica, silicate, orthosilicate, Si/Al compositions and like silica material has the desired physicochemical properties and is highly active and selective for making DMC from methanol and $CO_2$ in presence of a dehydrating or water trapping compound selected from organic nitriles, more preferably 2-cyanopyridine (2-CP).

In another embodiment, the catalyst of the invention is stable for several hours in a continuous flow operation. Catalyst formulations can be accomplished with active component and several reducible or non-reducible oxides. It is surprising to find that a formulation made out of mixed oxides of Ce and silica compound shows remarkably stable catalytic performance in the continuous production of DMC from methanol and $CO_2$ in presence of a dehydrating or water trapping compound.

Figure 4:
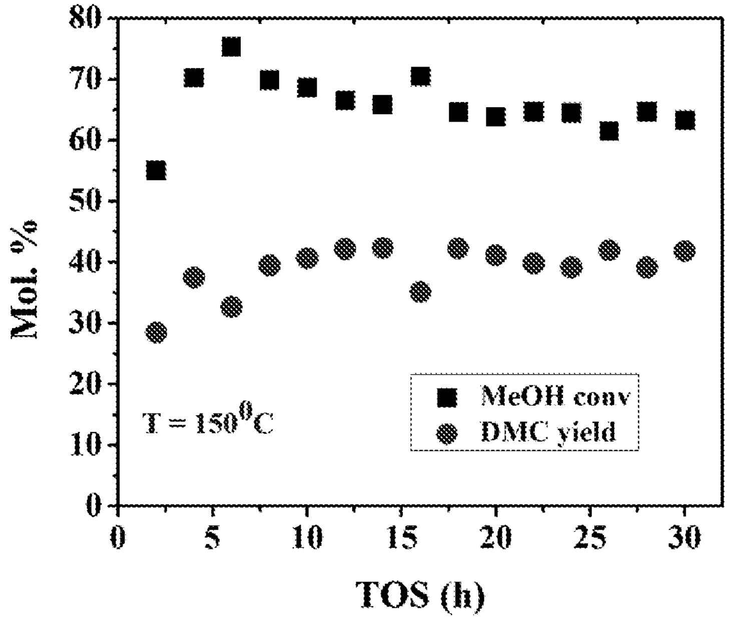
FIG. 4: Catalytic activity data as a function of reaction time for the reaction of methanol with $CO_2$ in a fixed-bed reactor over Zr—$CeO_2/SiO_2$ (Catalyst #1). Reaction conditions: catalyst=6.3 g, catalyst bed height=5 cm, reaction temperature=150° C., reactor pressure=30 bar $CO_2$, methanol:$CO_2$ molar ratio=1:2.1, 2-CP:methanol molar ratio=1:2, LHSV=2.5 $hour^{-1}$, GHSV ($CO_2$)=1250 $hour^{-1}$.
Figure 5:
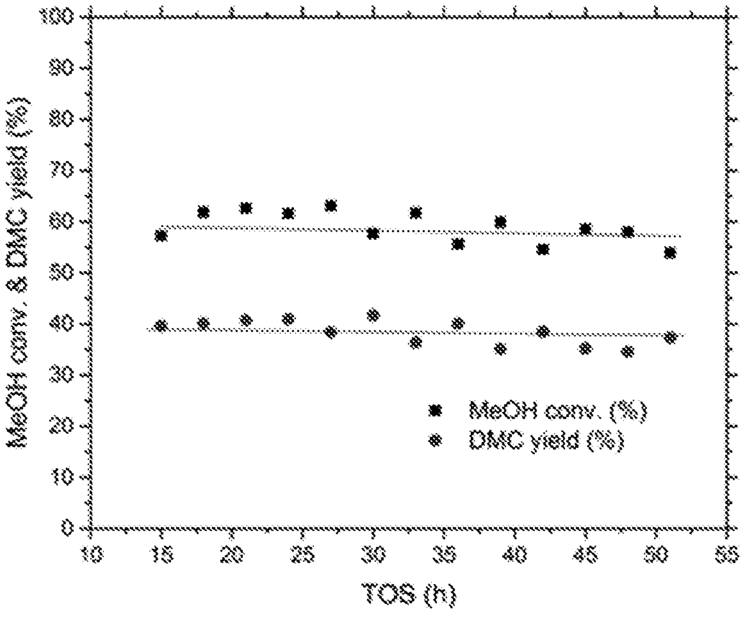
FIG. 5: Time-on-stream catalytic activity data for the reaction of methanol with $CO_2$ in presence of 2-cyanopyridine (2-CP) over Zr—$CeO_2/SiO_2$ (Catalyst #3) in a fixed-bed reactor. Reaction conditions: catalyst=7.6 g (4 cc), bed height of catalyst=3 to 4 cm, combined bed height of catalyst and diluents=10 cm, reaction temperature=150° C., reactor pressure=30 bar $CO_2$, methanol:$CO_2$ molar ratio=1:1, 2-CP:methanol molar ratio=1:2, LHSV=2.5 $hour^{-1}$, GHSV ($CO_2$)=630 $hour^{-1}$.
Figure 7:
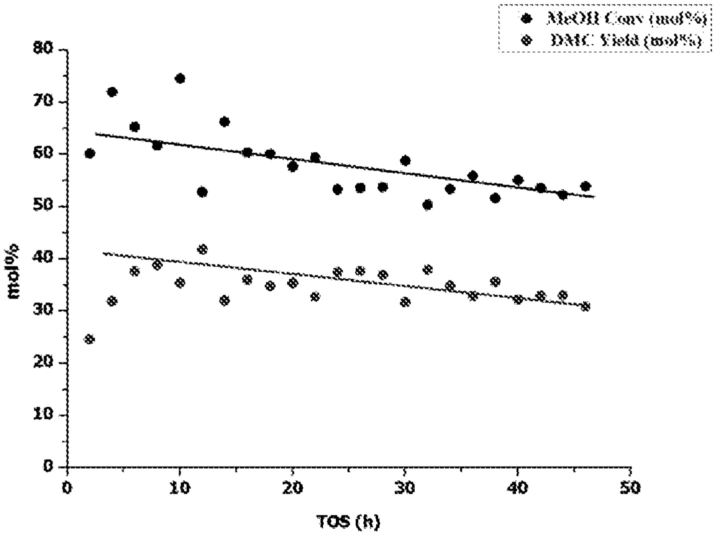
FIG. 7: Catalytic activity data as a function of time for the reaction of methanol with $CO_2$ over self-bound Zr—$CeO_2$ (Catalyst #5) in a fixed-bed reactor. Reaction conditions: catalyst=7.5969 g, bed height (catalyst+diluents)=10 cm, reaction temperature=150° C., reactor pressure=30 bar $CO_2$, methanol:$CO_2$ molar ratio=1:1, 2-CP:methanol molar ratio=1:2, LHSV=2.5 hour$^{-1}$, GHSV ($CO_2$)=625 hour$^{-1}$.

In a comparative embodiment, the stability of the self-bound extrudate catalyst of example 5 (Catalyst #5) is depicted in example 13 and FIG. 7, while the enhanced stability of the catalysts of the current invention i.e. Catalyst #1 and Catalyst #3 is depicted in FIGS. 4 and 5.

EXAMPLES

Following examples are given by way of illustration and therefore should not be construed to limit the scope of the invention.

Example 1

This example reports the synthesis procedure of cylindrical extrudates of Zr—$CeO_2$/$SiO_2$ (herein after referred as Catalyst #1) employing ethyl silicate as silica source. Firstly, Zr—$CeO_2$ mixed oxide was prepared as follows: Solution-A was prepared by dissolving 62.6 g of $Ce(NO_3)_3{\cdot}6H_2O$ and 3.7 g of $ZrO(NO_3)_2{\cdot}xH_2O$ in 1920 ml of water while stirring. Solution-B was prepared by dissolving 78.4 g of ammonium bicarbonate, $(NH_4)HCO_3$ in 640 ml of water while stirring till a clear solution formed. Solution-B was added to Solution-A over 30 min while stirring. The suspension was allowed to age at room temperature (25° C.) for 2 hours under stirring condition. The solid formed was separated by centrifugation/filtration and washed with 2.5% ethanol in water solution (4000 ml). It was dried at 80° C. for 24 hours and calcinied at 600° C. for 5 hours. Yield of Zr—$CeO_2$ mixed oxide recovered was 24 g. Then, the mixed oxide powder was added to ethyl silicate (in 82.5:17.5 weight ratio of mixed oxide to ethyl silicate). It was aged at 25° C. till dough-like paste formed which was then shaped into cylindrical extrudates (2 mm diameter) using an extruder, dried at 25° C. for 16 hours and calcinied at 550° C. for 5 hours. The catalyst thus formed was referred as Catalyst #1.

Example 2

This example reports the synthesis procedure of Zr—Ga—$CeO_2$/$SiO_2$ extrudates (hereafter referred as Catalyst #2). Firstly, Zr—Ga—$CeO_2$ mixed oxide was prepared, in which, Solution-A was prepared by dissolving 62.6 g of $Ce(NO_3)_3{\cdot}6H_2O$, 1.48 g of $ZrO(NO_3)_2{\cdot}xH_2O$ and 2.457 g of $Ga(NO_3)_3{\cdot}xH_2O$ in 1920 ml of water by stirring for 10 min. Solution-B was prepared by dissolving 78.5 g of ammonium bicarbonate in 640 ml of water by stirring for 10 min till a clear solution formed. Solution-B was added to solution-A over a period of 30 min. The resulting suspension was stirred for another 2 hours at room temperature (25° C.). The solid formed was separated by filtration and washed several times with 2.5% ethanol in water solution (4,000 ml). It was dried at 80° C. in an oven for 24 hours and calcinied in a muffle furnace (in air) at 500° C. for 3 hours. Yield of Zr—Ga—$CeO_2$ obtained was 24.5 g. The Zr—Ga—Ce mixed oxide powder and ethyl silicate in 82.5:17.5 weight ratio was mixed. It was aged at 25° C. till dough-like paste formed which was then, shaped into extrudates of 2 mm diameter using an extruder. The material was dried at 25° C. for 16 hours and calcinied at 550° C. for 5 hours. The material thus formed was labeled as Catalyst #2.

Example 3

This example provides the preparation method of trilobes of Zr—$CeO_2$/$SiO_2$ (hereafter referred as Catalyst #3) employing colloidal silica as silica source. In typical synthesis, Solution-A was prepared dissolving 183.463 g of $Ce(NO_3)_3{\cdot}6H_2O$ and 10.873 g of $ZrO(NO_3)_2{\cdot}xH_2O$ in 5625 ml of $H_2O$ while stirring for 30 min. Solution-B was prepared by dissolving 229.75 g of ammonium bicarbonate $(NH_4)HCO_3$ in 1875 ml of water by stirring until a clear solution was observed. Then, Solution-B was added dropwise to Solution-A with constant stirring. The stirring was continued for another 30 min at room temperature (25° C.). The resulting suspension was taken into a partially closed flask and aged for 2.5 hours at 95° C. (placing in a temperature-controlled oil bath) while stirring at a speed of 230 rpm. After the heat treatment, the precipitate was filtered and washed with 2.5% ethanol in water solution. The solid obtained was dried at 110° C. for 16 hours and calcinied in the presence of air at 550° C. for 4 hours. The yield of Zr—$CeO_2$ mixed oxide powder recovered was 75 g. It was converted into dough by adding about 30 ml of 40% colloidal silica. Trilobes of this material were formed using an extruder. They were dried at 110° C. for 12 hours and calcinied in air at 550° C. The material thus prepared was designated as Catalyst #3. X-ray photoelectron spectroscopy revealed that the content of reduced Ce ions ($Ce^{3+}$) in this sample is 14.5% and the ratios of $Ce^{4+}/Ce^{3+}$=5.89.

Example 4

This example provides the preparation method of trilobes of Zr—$CeO_2/Al_2O_3$ (hereafter referred as Catalyst #4). In typical synthesis, Solution-A was prepared dissolving 183.463 g of $Ce(NO_3)_3·6\ H_2O$ and 10.873 g of $ZrO(NO_3)_2·xH_2O$ in 5625 ml of $H_2O$ while stirring for 30 min. Solution-B was prepared by dissolving 229.75 g of $(NH_4)HCO_3$ in 1875 ml of water by stirring until a clear solution was observed. Then, Solution-B was added drop-wise to Solution-A with constant stirring. The stirring was continued for another 30 min at room temperature (25° C.). The resulting suspension was taken into a partially closed flask and aged for 2.5 hours at 95° C. (placing in a temperature-controlled oil bath) while stirring at a speed of 230 rpm. After the heat treatment, the precipitate was filtered and washed with 2.5% ethanol in water solution. The solid obtained was dried at 110° C. for 16 hours and calcinied in the presence of air at 550° C. for 4 hours. The yield of Zr—$CeO_2$ mixed oxide powder recovered was 75 g. It was converted into dough by adding pseudo-boehmite calcimined at 900° C. (Zr—$CeO_2$ powder:$Al_2O_3$ mass ratio=80:20) and 5% acetic acid solution. Trilobes of this material were formed using an extruder. They were dried at 110° C. for 12 hours and calcined in air at 550° C. The material thus prepared was designated as Catalyst #4.

Example 5

This example provides the preparation method of Zr—$CeO_2$ and its shaped form (hereafter referred as Catalyst #5) via., self-binding using acetic acid as peptizing agent. In a typical preparation, cerium nitrate (244.6 g) and zirconyl nitrate (14.5 g) were dissolved in 7500 ml of de-mineralized water (Solution-A). $(NH_4)HCO_3$ (306.3 g) was dissolved in 2500 ml of de-mineralized water (Solution-B). Solution-B was added drop-wise to Solution-A with constant stirring over a period of 30 min. The suspension was kept for aging at room temperature (25° C.) for 2 hours while stirring. The solid was separated by centrifugation and washed with 2.5% ethanol solution (16,000 ml). It was dried at 80° C. for 1 day and calcinied at 600° C. for 5 hours. The obtained mixed oxide powder was converted in dough by adding 5% acetic acid solution and shaped into trilobes using an extruder, followed by drying at 110° C. for 12 hours and calcining at 550° C. for 5 hours. The material thus prepared was labeled as Catalyst #5.

Example 6

This comparative example provides the preparation method of cylindrical extrudates of $CeO_2/SiO_2$ (hereafter referred as Catalyst #6). Commercial $CeO_2$ powder (with no pre-activation) and tetraethyl orthosilicate (TEOS) in 82.5:17.5 weight ratio were mixed. It was aged at room temperature (25° C.) till suitable dough-like paste formed. Then, it was shaped into cylindrical extrudates (of 2 mm diameter) using an extruder, dried at 25° C. for 16 hours and calcinied at 550° C. for 5 hours. The material thus prepared was labeled as Catalyst #6.

Example 7

This comparative example provides the preparation method of cylindrical extrudates of $CeO_2/Al_2O_3$ (hereafter referred as Catalyst #7). Commercial $CeO_2$ powder (without any pre-treatment) and pseudo-boehmite in 80:20 weight ratio were mixed in presence of a small quantity of water or 5% acetic acid solution till a suitable dough formed. Then, it was extruded (2 mm diameter), dried at room temperature (25° C.) for 24 hours and calcinied at 550° C. for 5 hours. The material thus prepared was labeled as Catalyst #7.

Example 8

This example reports the synthesis procedure of Zr—Ga—$CeO_2$ powder (hereafter referred as Catalyst #8). Solution-A was prepared by dissolving 1.9540 g of $Ce(NO_3)_3·6H_2O$, 0.0462 g of $ZrO(NO_3)_2·xH_2O$ and 0.0767 g of $Ga(NO_3)_3·xH_2O$ in 60 ml of water by stirring for 10 min. Solution-B was prepared by dissolving 2.4507 g of ammonium bicarbonate in 20 ml of water by stirring for 5 min. Solution-B was added drop-wise to solution-A over a period of 30 min. The resulting was stirred for another 2 hours at 25° C. The solid formed was separated by filtration and washed several times with 2.5% ethanol in water solution (375 ml). It was dried at 80° C. in an oven for 24 hours and calcinied in a muffle furnace (in air) at 500° C. for 3 hours. The mixed oxide material thus formed was labeled as Catalyst #8.

Example 9

This example reports the synthesis procedure of Zr—$CeO_2$ powder (hereafter referred as Catalyst #9). Solution-A was prepared by dissolving 1.9540 g of $Ce(NO_3)_3·6H_2O$ and 0.1159 g of $ZrO(NO_3)_2·xH_2O$ in 60 ml of water by stirring. Solution-B was prepared by dissolving 2.4507 g of ammonium bicarbonate in 20 ml of water by stirring. Solution-B was added drop-wise to solution-A over a period of 30 min. The resulting was stirred for another 2 hours at 25° C. The solid formed was separated by centrifugation and washed with 2.5% ethanol in water solution (125 ml). It was dried at 80° C. in an oven for 24 hours and calcinied in a muffle furnace (in air) at 600° C. for 5 hours. The mixed oxide material thus formed was labeled as Catalyst #9.

Example 10

This example provides the experimental procedure for evaluation of shaped catalysts (#1, #6 and #7) in the reaction of methanol (MeOH) with $CO_2$ in presence of 2-cyanopyridine (2-CP) as dehydrating or water-trapping compound. The experiments were performed in a fixed-bed, down-flow stainless steel reactor (FIG. 1). The reactor tube had the following dimensions: internal diameter=1.5 cm, outer diameter=1.9 cm and length=30 cm. Sized catalyst extrudate beads (diameter=2 mm and length=3 mm) were placed in an isothermal zone of the reactor with a sufficient layer of inert material near inlet to ensure proper pre-heating and distribution of feed before it reaches the catalyst zone. Typically, about 6.3 g of catalyst extrudes (with catalyst volume=4.8 ml and bed height of about 5 cm) were loaded in the reactor. The loaded catalyst was activated in nitrogen at 200° C. for 5 hours.

Figure 2:
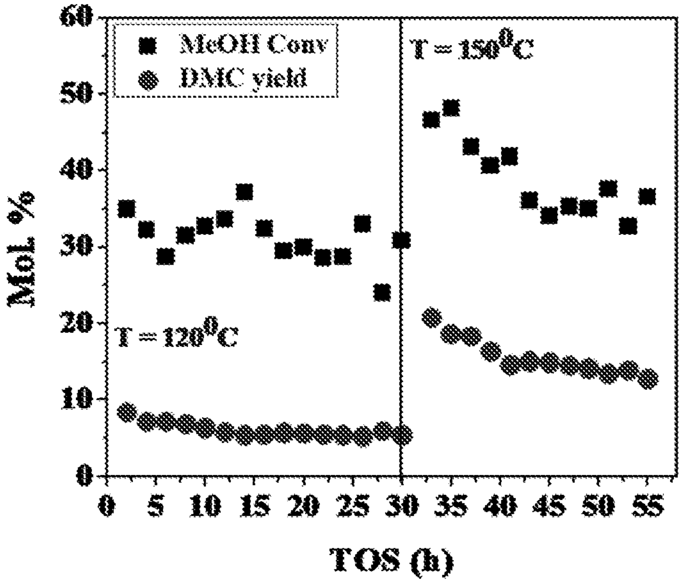
FIG. 2: Catalytic activity data as a function of time in a fixed-bed reactor for the reaction of methanol with $CO_2$ over $CeO_2/Al_2O_3$(Catalyst #7). Reaction conditions: catalyst=6.3 g, catalyst bed height=5 cm, reaction temperature=120° C. or 150° C., reactor pressure=30 bar $CO_2$, methanol:$CO_2$ molar ratio=1:2.1, 2-CP:methanol molar ratio=1:2, LHSV=2.5 $hour^{-1}$, GHSV ($CO_2$)=1250 $hour^{-1}$.
Figure 3:
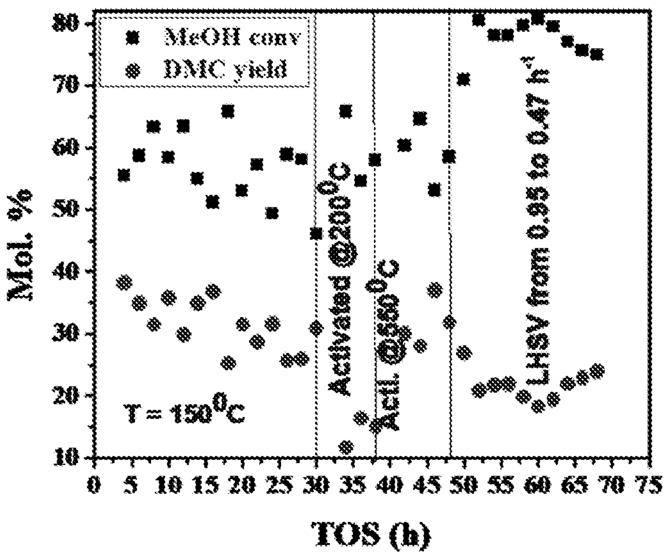
FIG. 3: Catalytic activity data as a function of time for the reaction of methanol with $CO_2$ in a fixed-bed reactor over $CeO_2/SiO_2$ (Catalyst #6). Reaction conditions: catalyst=6.3 g, catalyst bed height=5 cm, reaction temperature=150° C., reactor pressure=30 bar $CO_2$, methanol:$CO_2$ molar ratio=1:2.1, 2-CP:methanol molar ratio=1:2, LHSV=2.5 $hour^{-1}$, GHSV ($CO_2$)=1250 $hour^{-1}$.

The system was pressurized up to 30 bar with $CO_2$ and the temperature was allowed to reach desired value (120-150° C.). The mixture of MeOH and 2-CP (in molar ratio of 2:1)

was pumped into the reactor using a high-performance liquid chromatography pump (HPLC pump) (at a flow rate of methanol=4.24 g/hour and 2-CP=6.92 g/hour; density of feed solution=0.93 g/ml; LHSV=2.5 hour$^{-1}$). $CO_2$ gas flow rate was 100 ml/min (GHSV=1250 hour$^{-1}$). Liquid mass balance was more than 98%. To 8 ml of the product, 30 ml of ethanol and 0.202 g of nonane-1-ol were added as a solvent and internal standard, respectively. It was stirred for 10 min till the solid dissolved and a liquid was a clear solution. It was analyzed with the help of a Varian 3400 GC equipped with a flame ionization detector and CP-SIL5CB column (60 m-long×0.32 mm-i.d.×0.25 μm-film thickness). Injector port temperature=column temperature=detector port temperature=270° C. Injection volume=1 microliter. GC program: 40° C. to 80° C. @ 10° C./min, hold for 6 min and then 80° C. to 270° C. @ 20° C./min and hold for 8 min. The results of the catalytic activity and observations are listed in Table 1. Catalytic activity data as a function of time are presented in FIGS. 2 to 4.

TABLE 1

Comparative catalytic activity data for the reaction of methanol with $CO_2$

| Catalyst | Reaction temperature (° C.) | Yield of DMC (mol %) At 3 hours | Yield of DMC (mol %) At the end | Observation |
|---|---|---|---|---|
| Catalyst #7 | 120 | 8 | 4.5 (after 30 hours) | Unstable |
| Catalyst #7 | 150 | 22 | 13.2 (after 20 hours) | Unstable |
| Catalyst #6 | 150 | 38 | 24 (after 32 hours) | Unstable |
| Catalyst #1 | 150 | 40 | 40 (after 30 hours) | Stable |

Example 11

This example provides the experimental procedure for the evaluation of shaped Catalysts #3 in the reaction of methanol (MeOH) with $CO_2$ in presence of 2-cyanopyridine (2-CP) as dehydrating or water-trapping compound. The experiments were performed in a fixed-bed, down-flow stainless steel reactor. The reactor tube had the following dimensions: internal diameter=1.57 cm and length=62 cm. The catalyst was placed in an isothermal zone of the reactor with a sufficient layer of inert material near inlet to ensure proper pre-heating and distribution of feed before it reaches the catalyst zone. During the loading process, the catalyst was typically divided into multiple beds. Following each bed of the catalyst, silicon carbide (80-120 mesh) was packed into the void spaces of the catalyst bed to ensure uniformity in gas-liquid flow distribution. Typically, about 4 cc of sized catalyst trilobes (1.5 mm diameter and 0.5 to 2 cm length) were loaded into the reactor. Catalyst bed height was about 3 to 4 cm. The loaded catalyst was activated in helium flow at 170 ml/min (200° C. for 7 hours). The system was pressurized up to 30 bar with $CO_2$ (GHSV=630 hour$^1$) and the temperature was allowed to reach 150° C. The mixture of MeOH+2-CP (in molar ratio of 2:1) was pumped into the reactor using a high-performance liquid chromatography pump (HPLC pump) at a flow rate of 0.15 ml/min. $CO_2$ gas flow was 42 ml/min and overall liquid hourly space velocity (LHSV) of the feed (MeOH+2-CP) was 2.25 hour$^{-1}$. To 8 ml of the product, 30 ml of ethanol and 0.202 g of nonane-1-ol were added as a solvent and internal standard, respectively. It was stirred for 10 min till the solid dissolved and the liquid obtained was a clear solution. It was analyzed with the help of a Varian 3400 GC equipped with a flame ionization detector and CP-SIL5CB column (60 m-long×0.32 mm-i.d.×0.25 μm-film thickness). Injector port temperature=column temperature=detector port temperature=270° C. Injection volume=1 microliter. GC program: 40° C. to 80° C. @ 10° C./min, hold for 6 min and then, 80° C. to 270° C. @ 20° C./min and hold for 8 min. Methanol conversion of 63 mol % and DMC yield of 40 mol % were obtained. 2-CP conversion of 52 mol % and 2-picolinamide (2-PA) yield 46% was observed. The catalytic activity (methanol conversion and DMC yield) was stable over a period of 60 hours in a continuous run (FIG. 5).

Example 12

Figure 6:
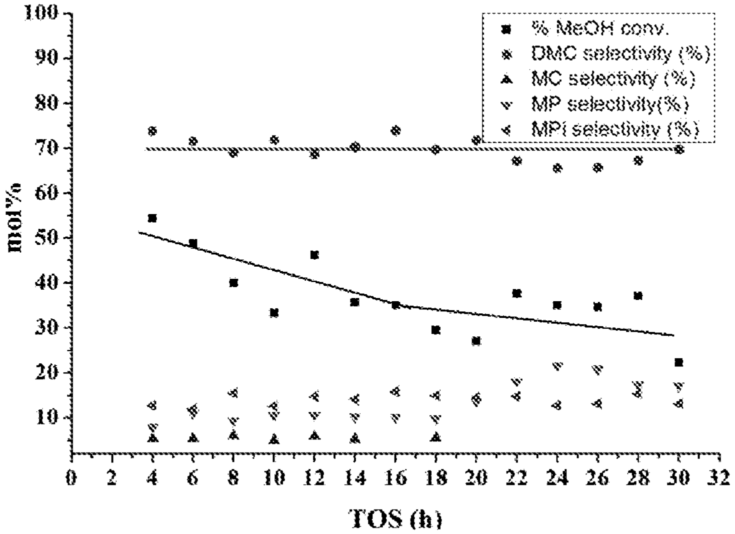
FIG. 6: Time-on-stream catalytic activity data for the reaction of methanol with $CO_2$ in presence of 2-cyanopyridine (2-CP) over Zr—$CeO_2/Al_2O_3$ (Catalyst #4) in a fixed-bed reactor. Reaction conditions: catalyst=7.09 g, silicon carbide diluents=7.21 g, bed height (catalyst+diluents)=8 cm, reaction temperature=150° C., reactor pressure=30 bar $CO_2$, methanol:$CO_2$ molar ratio=1:1, 2-CP:methanol molar ratio=1:2, LHSV=2.5 $hour^{-1}$, GHSV ($CO_2$)=625 $hour^{-1}$.

This example provides the experimental procedure for the evaluation of shaped catalyst #4 in the reaction of methanol (MeOH) with $CO_2$ in presence of 2-cyanopyridine (2-CP) as dehydrating or water-trapping compound. The experiments were performed in a fixed-bed, down-flow stainless steel reactor. The reactor tube had the following dimensions: internal diameter=1.5 cm, outer diameter=1.9 cm and length=32 cm. The catalyst was placed in an isothermal zone of the reactor with a sufficient layer of inert material near inlet to ensure proper pre-heating and distribution of feed before it reaches the catalyst zone. During the loading process, the catalyst was typically broken into uniform beds of diameter=2 mm and length=3 mm. Silicon carbide (80-120 mesh) was used as a diluent to ensure uniformity in gas-liquid flow distribution. Typically, about 7.09 g (4.8 cc) of catalyst trilobes and 7.21 g (4.8 ml) of silicon carbide diluent were loaded into the reactor. The bed height (catalyst+diluents) was 8 cm. The loaded catalyst was activated in nitrogen at 200° C. for 5 hours. The system was pressurized up to 30 bar with $CO_2$ and the temperature was allowed to reach 150° C. The mixture of MeOH+2-CP (in molar ratio of 2:1) was pumped (0.2 ml/min) into the reactor using a high-performance liquid chromatography pump (HPLC pump) (LHSV=2.5 hour$^{-1}$). $CO_2$ gas flow was 50 ml/min (GHSV=625 hour$^{-1}$). The continuous run was conducted for 30 hours. Methanol conversion decreased over 30 hours from 55 to 24 mol % and DMC yield decreased from 39 to 17 mol % with the selectivity being about 70 mol % (FIG. 6).

Example 13

This example provides the experimental procedure for the evaluation of shaped catalyst #5 in the reaction of methanol (MeOH) with $CO_2$ in presence of 2-cyanopyridine (2-CP) as dehydrating or water-trapping compound. The experiments were performed in a fixed-bed, down-flow stainless steel reactor. The reactor tube had the following dimensions: internal diameter=1.5 cm, outer diameter=1.9 cm and length=32 cm. The catalyst was placed in an isothermal zone of the reactor with a sufficient layer of inert material near inlet to ensure proper pre-heating and distribution of feed before it reaches the catalyst zone. During the loading process, the catalyst was typically broken into uniform beds of diameter=3 mm and length=4 mm. Silicon carbide (80-120 mesh) was used as a diluent to ensure uniformity in gas-liquid flow distribution. Typically, about 7.5969 g (4.8 ml) of catalyst and 6.5578 g (4.8 ml) of ceramic ball diluent were loaded into the reactor. The bed height (catalyst+diluents) was 10 cm. The loaded catalyst was activated in nitrogen at 200° C. for 5 hours. The system was pressurized up to 30 bar with $CO_2$ and the temperature was allowed to reach desired reaction temperature. The mixture of MeOH+

2-CP (in molar ratio of 2:1) was pumped (0.2 ml/min) into the reactor using a high-performance liquid chromatography pump (HPLC pump; LHSV=2.5 hour$^{-1}$). $CO_2$ gas flow was 50 ml/min (GHSV=625 hour$^1$). Reaction temperature was 130° C. for the initial 25 hours and then 140° C. for another 25 hours. Methanol conversion decreased from 65 to 53 mol % and DMC yield decreased from 39 to 32 mol % in 48 hours (FIG. 7).

Example 14

This example reports the catalytic performance of mixed oxides (Catalysts #8 and #9) in a batch reactor. The reaction was conducted in a 100 cc stainless-steel Parr high pressure autoclave equipped with a magnetic drive stirrer, thermocouple and programmable controller unit. 3.2 g of methanol, 5.2 g of 2-cyanopyridine (2-CP) and 0.1 g of catalyst powder were taken in the reactor which was later pressurized with $CO_2$ to 5 MPa at 25° C. The temperature of the reactor was raised to 120° C. and the reaction was conducted while stirring at a speed of 600 rpm for 12 hours. At the end of the reaction, the reactor was cooled to 25° C. and unreacted $CO_2$ was vented out. Then, 30 ml of ethanol and 0.202 g of nonane-1-ol were added as a solvent and internal standard, respectively. The contents of the reactor were stirred for 10 min to dissolve the solid organic product completely in the liquid portion. The contents were transferred to the centrifuge tube. The catalyst was separated from the liquid products by centrifugation/decantation. The liquid products were analyzed and quantified with the help of a Varian 3400 GC equipped with a flame ionization detector and CP-SIL5CB column (60 m-long×0.32 mm-i.d.×0.25 μm-film thickness). Injector port temperature=column temperature=detector port temperature=270° C. Injection volume=1 microliter. GC program: 40° C. to 80° C. @ 10° C./min, then hold for 6 min. Later, 80° C. to 270° C. @ 20° C./min and hold for 8 min. The results are presented in Table 2.

TABLE 2

Catalytic activity data of Zr—$CeO_2$ and Zr—Ga—$CeO_2$ in batch reactor

| Catalyst | Methanol conversion(mol %) | DMC yield (mol %) |
|---|---|---|
| Catalyst #8 | 71.9 | 60.7 |
| Catalyst #9 | 77.1 | 71.7 |

Physicochemical characteristics of the shaped catalysts prepared in Examples 1 to 9 are listed in Table 3. SEM image showing typical morphology of cerium-based mixed oxide component in Catalyst #3 is depicted in FIG. 8.

TABLE 3

Physiochemical properties of the catalysts

| Catalyst | Specific surface area ($S_{BET}$; $m^2$/g) | Pore volume (cc/g) | Average pore size (nm) | Acidity (mmol/g) | Basicity (mmol/g) | Crushing strength (Newton) | Water adsorption capacity (wt %) |
|---|---|---|---|---|---|---|---|
| Catalyst #1 | 149 | 0.18 | 2.5 | | | | 2.5 |
| Catalyst #3 | 113 | 0.17 | 6.0 | 0.28 | 0.26 | 5.4 | 1.5 |
| Catalyst #5 | 49 | 0.08 | — | 0.14 | 0.068 | 2.2 | |
| Catalyst #6 | 147 | 0.24 | 5.7 | 0.29 | 0.10 | 3.7 | |
| Catalyst #7 | 84 | 0.14 | 3.4 | 0.16 | 0.10 | 3.9 | |

Advantages of the Invention

Highly stable catalyst under the reaction conditions of DMC synthesis.

Continuous flow process for making DMC.

Heterogeneous, bifunctional, hydrophobic catalyst-based industrially feasible process.

Economically beneficial, sustainable process for DMC.

Used catalyst can be reactivated or regenerated by known procedures of solvent wash and activation in air or oxygen atmosphere at high temperature.

We claim:

1. A continuous process for synthesis of dimethyl carbonate (DMC), said process comprising contacting methanol with $CO_2$ over a catalyst formulation; at a reaction temperature in a range of 120 to 160° C.; for a reaction time period in a range of 2 to 10 hours; reaction pressure in a range of 30 to 100 bar in the presence of an organic nitrile dehydrating or water trapping compound, wherein the catalyst formulation has at least 30 hours of catalytic stability; and wherein said catalyst formulation comprises:

(a) mixed oxides of cerium (Ce) with other elements selected from the group consisting of zirconium (Zr), lanthanum (La), gallium (Ga) and combinations thereof and the metal oxides have an elongated hexagonal, spindle-shaped, rod-like or spherical morphology; and (b) a form of silica ($SiO_2$) selected from the group consisting of colloidal silica, silicate, orthosilicate, Si/Al combinations and silica source material wherein the silica content in the catalyst formulation is in the range of 2 to 25 weight percent, and content of Ce-oxide in the mixed oxide portion is in the range of 50 to 95 mole percent;

(c) wherein the hydrophobicity, represented by water adsorption capacity, is less than 10 weight percent of the catalyst, the crush strength of the catalyst is 2 to 7 Newton, and acidity/basicity molar ratio of the bifunctional catalyst is in the range of 0.5 to 2.5.

2. The process as claimed in claim 1, wherein molar ratio of methanol to dehydrating or water trapping compound is in the range of 1:1 to 3:1; and molar ratio of methanol to carbon dioxide is in the range of 1:3 to 2:1.

3. The process as claimed in claim 1, wherein the dehydrating or water trapping compound is 2-cyanopyridine (2-CP).

4. The process as claimed in claim 1, wherein flow rate of liquid feed containing methanol and dehydrating or water trapping compound that is expressed in terms of liquid hourly space velocity (LHSV) is in the range of 0.5 to 4 hour$^{-1}$.

5. The process as claimed in claim 1, wherein flow rate of carbon dioxide that is expressed in terms of gas hourly space velocity (GHSV) is in the range of 400 to 1000 $hour^{-1}$.

6. The process as claimed in claim 1, wherein said process is performed in a fixed-bed reactor, continuous stirred tank reactor or continuous-flow reactors.

7. The process as claimed in claim 1, wherein the yield of dimethyl carbonate is above 30 mole percent.

8. A catalyst formulation for a continuous process for synthesis of dimethyl carbonate, wherein said catalyst formulation comprises:

(a) mixed oxides of cerium (Ce) with other elements selected from the group consisting of zirconium (Zr), lanthanum (La), gallium (Ga) and combinations thereof and the metal oxides have an elongated hexagonal, spindle-shaped, rod-like or spherical morphology respectively, and (b) a form of silica ($SiO_2$) selected from the group consisting of colloidal silica, silicate, orthosilicate, Si/Al combinations and silica source material wherein the silica content in the catalyst formulation is in the range of 2 to 25 weight percent, and content of Ce-oxide in the mixed oxide portion is in the range of 50 to 95 mole percent;

(c) wherein the hydrophobicity, represented by water adsorption capacity, is less than 10 weight percent of the catalyst, the crush strength of the catalyst is 2 to 7 Newton, and acidity/basicity molar ratio of the bi-functional catalyst is in the range of 0.5 to 2.5.

9. The catalyst formulation as claimed in claim 8, wherein said catalyst formulation is selected from Zr—$CeO_2/SiO_2$, Zr—Ga—$CeO_2/SiO_2$, Zr—$CeO_2/Al_2O_3$, Zr—$CeO_2$, $CeO_2/SiO_2$, $CeO_2/Al_2O_3$, Zr—La—$CeO_2/SiO_2$, Ga—$CeO_2/SiO_2$, La—$CeO_2/SiO_2$, Zr—Ga—$CeO_2/SiO_2$, Zr—Ga—$CeO_2/SiO_2$—$Al_2O_3$, Ga—$CeO_2/SiO_2$—$Al_2O_3$, La—$CeO_2/SiO_2$—$Al_2O_3$ and Zr—La—$CeO_2/SiO_2$—$Al_2O_3$.

10. The catalyst formulation as claimed in claim 8, wherein said catalyst formulation is shaped and formed into extrudates, trilobes, spheres or tablets.

11. The catalyst formulation as claimed in claim 8, wherein the part of cerium ions in said catalyst formulation is in partially reduced (+3) oxidation state.

12. The catalyst formulation as claimed in claim 8, wherein said catalyst formulation has specific surface area in the range of 100 to 300 $m^2/g$ and pore volume in the range of 0.1 to 0.35 cc/g.

13. A process of preparing a catalyst formulation as claimed in claim 8, wherein said process comprises:

(a) co-precipitating precursor salt solutions of Ce and other element (Zr, La, Ga or combinations thereof) sequentially or once through at a temperature in the range of 20° C. to 30° C. using a precipitating agent;

(b) mixing and ageing of the suspension of step (a) at a temperature in the range of 30° C. to 120° C.;

(c) filtering and water washing of the formed precipitate;

(d) drying the precipitate of step (c) at 25° C. to 100° C. followed by calcination at a temperature in the range of 400° C. to 600° C. to obtain mixed oxide catalyst; and (e) mixing the mixed oxide catalyst obtained of step (d) with a silica source selected from colloidal silica, ethyl silicate, ethyl orthosilicate, and Si/Al combination silica source and formulating and shaping the catalyst.

14. The process as claimed in claim 13, wherein the precipitating agent used in step (a) is selected from the group consisting of urea, sodium hydroxide, ammonium hydroxide, ammonium bicarbonate, tetraalkylammonium hydroxide, and the precursor salts are selected from the group consisting of $Ga(NO_3)_3 \cdot xH_2O$, galium halide, $Ce(NO_3)_3 \cdot 6H_2O$, cerius sulphate, cerium oxalate, $ZrO(NO_3)_2 \cdot xH_2O$, $Zr(SO_4)_2$, zirconium alkoxide, zirconium halide, lanthanum nitrate, lanthanum halide and lanthanum carbonate.

* * * * *